United States Patent [19]

Edwards

[11] Patent Number: 4,703,264
[45] Date of Patent: Oct. 27, 1987

[54] SELF-ORIENTING CONDUIT PROBE
[75] Inventor: Lawrence J. Edwards, Suffield, Conn.
[73] Assignee: Combustion Engineering, Inc., Windsor, Conn.
[21] Appl. No.: 732,999
[22] Filed: May 13, 1985
[51] Int. Cl.[4] .................... G01N 27/87; G01R 33/00
[52] U.S. Cl. .................................... 324/220; 33/542; 122/504; 165/76; 165/11.2; 324/262
[58] Field of Search ................................ 324/219–221, 324/228, 207, 208, 226, 227, 237, 238, 240, 241–243, 347, 338, 339, 202; 33/178 F, 143 L, 149 J, 542, 544; 73/104, 105, 86; 104/138 G; 128/4, 6; 122/379, 504; 165/11.2, 76

[56] References Cited

U.S. PATENT DOCUMENTS

| | | | |
|---|---|---|---|
| 3,149,277 | 9/1964 | Bennett et al. | 324/347 |
| 3,237,093 | 2/1966 | Bennett et al. | 324/347 |
| 3,789,511 | 2/1974 | Groom et al. | 33/542 X |
| 3,906,358 | 9/1975 | Stone | 324/220 |
| 3,916,302 | 10/1975 | Madewell | 324/220 |
| 4,050,384 | 9/1977 | Chapman | 104/138 G |
| 4,319,191 | 3/1982 | Meador et al. | 324/341 |
| 4,413,231 | 11/1983 | Amedro et al. | 324/220 |
| 4,439,831 | 3/1984 | Sinclair | 324/339 X |

FOREIGN PATENT DOCUMENTS

| | | | |
|---|---|---|---|
| 2837488 | 12/1979 | Fed. Rep. of Germany | 324/219 |
| 0121790 | 9/1979 | Japan | 324/220 |
| 1488833 | 10/1977 | United Kingdom | 324/220 |
| 0903759 | 2/1982 | U.S.S.R. | 324/220 |

Primary Examiner—Reinhard J. Eisenzopf
Assistant Examiner—Warren S. Edmonds
Attorney, Agent, or Firm—John H. Mulholland

[57] ABSTRACT

A probe (10) for scanning the interior of a curved conduit (28) has a carrier (12) with a rotatable portion (12b). Sensor means (18) are secured to the rotatable portion (12b) and are aligned with respect to the curvature of the conduit by means of an elongated flat strip (20), secured to the rotatable portion (12b) and extending longitudinally therefrom. Driving means (14) is provided to urge the probe (10) longitudinally through the conduit (28).

4 Claims, 3 Drawing Figures

(54) SELF-ORIENTING CONDUIT PROBE

FIELD OF THE INVENTION

The present invention relates to a probe for traversing the interior of a curved conduit or the like, and more particularly, to a probe having the capacity to orient itself with respect to the plane of curvature of the conduit.

BACKGROUND OF THE INVENTION

Remote examination of tubular conduits is an activity well known in the chemical and power generation industries. Such industries utilize various conduit scanning methods in order to attempt to detect weaknesses or other potential failure points before an actual tube failure or leak situation occurs. Such early detection reduces unscheduled equipment outages, providing benefits in scheduling and overall cost savings.

It is well known that certain portions of a material-carrying conduit are more susceptible to wear, erosion, or other degradation and are therefore scanned with greater interest than other, less failure-prone portions. For example, in a nuclear steam generator utilizing a flow of heated primary fluid through a bundle of tubes in the shape of an inverted U for heating a surrounding secondary fluid, it is the curved portion of the tubular conduits which is most susceptible to corrosion or other degradation.

It has moreover been found that within the curved portion the innermost and outermost sections of the conduit wall are the areas in which stress cracking or corrosion are most likely to occur. It is therefore desirable to concentrate any scanning effort on the innermost and outermost radial portion of the conduit with respect to the axis of curvature. In order to provide this type of scan, probes have been utilized which traverse the interior of the individual conduits, each probe bearing one or more sensor means for determining the quality and status of the conduit wall. As the interior of the tubular conduits in a nuclear steam generator do not contain any reference points usable to orient such a probe, it has often been the practice to utilize multiple sensors spaced radially about the probe or to conduct repetitive scans of the curved conduit portion in order to increase the likelihood that the critical innermost and outermost conduit wall portions have been examined. As will be appreciated by those skilled in the art, the linear vertical portions of such inverted U tubes may be 30 feet in length or greater, thus making any attempt to orient the sensor probe by means of the driving cable a practical impossibility.

The use of multiple sensors, while increasing the area scanned, requires significantly greater effort to interpret the results of the individual sensors, due to the increased volume of data collected (much of which is not of interest). The use of multiple passes with a single sensor results in the same production of an abundance of scanning data and includes the additional disadvantage of possibly missing a critical portion of the conduit under consideration.

An effective device for scanning a curved conduit such as described above would orient the sensing means so as to pass over the desired portions of the conduit wall in a sensing relationship on the first pass therethrough, eliminating the need for multiple scans as well as the possibility that a critical portion of the conduit wall might not be measured.

SUMMARY OF THE INVENTION

The present invention solves the problem of determining and maintaining probe sensor orientation in a curved portion of a steam generator tube or the like by providing an elongated, flat strip of resilient material affixed to the probe carrier and having a first transverse bending moment significantly greater than a second, perpendicular transverse bending moment.

When inserted within a conduit, the flat strip precedes the probe as it is pushed longitudinally through the conduit. Upon encountering the curved segment, the flat strip will bend to conform thereto, rotating both itself and the probe carrier to minimize any bending about the first transverse axis, thus resulting in an orientation such that the first transverse axis is perpendicular to the plane of the curved conduit, and the second transverse axis lies in the plane of curvature.

The probe assembly includes sensor means, oriented by the interaction of the curved conduit section and the flat strip, for scanning those portions of the curved conduit wall that may be of interest as being particularly subject to wear or corrosion or other measurable conditions.

It is therefore an object of the probe according to the present invention to traverse the interior of a curved conduit.

It is further an object of the probe according to the present invention to be preferably aligned while traversing the curved section for bringing the probe sensors into a sensing relationship with those portions of the curved conduit wall which are of particular interest.

It is still further an object of the probe according to the present invention to accomplish this alignment without active participation by the probe operator and without the use of active electrical or other means for maintaining the probe sensors in alignment with respect to plane curvature of the conduit.

BRIEF DESCRIPTION OF THE DRAWING FIGURES

DESCRIPTION OF THE PREFERRED EMBODIMENT

Figure 1:
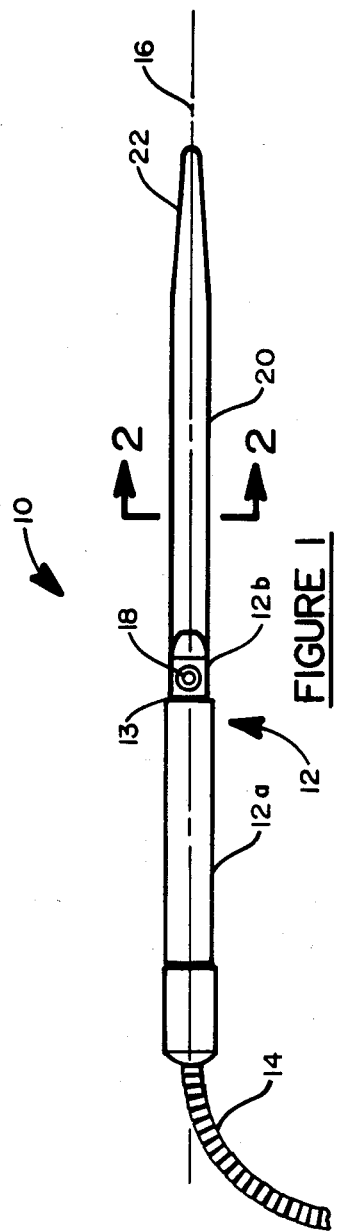
FIG. 1 shows a side view of a probe according to the present invention in a plane perpendicular to the first transverse axis.

Referring to the drawing figures, and in particular to FIG. 1 thereof, the preferred embodiment of the present invention is depicted as a probe assembly 10 having a carrier 12, being generally cylindrical in form and sized to be longitudinally slidable through the interior of a steam generator conduit or the like.

The carrier 12 is urged longitudinally through the conduit by urging means 14 shown in FIG. 1 as being a flexible cable 14 which possesses sufficient longitudinal rigidity and strength to enable an operator located at one end of the conduit to insert and drive the probe 10 through any desired length. The cable 14 is additionally flexible transversely and the carrier 12 is also sized so as to permit the probe 10 to negotiate any curves or other obstructions which may be present in the subject conduit.

Affixed to the carrier 12 are sensor means 18 for determining the condition of at least a portion of the conduit wall currently being traversed. The sensors 18 are preferably selected from a group of sensors having direction measuring capabilities, thus confining the measurements to only a predetermined sector of the tube or conduit circumference. Such sensors include those utilizing magnetic eddy currents, ultrasonic radiation, visual inspection, or any other sensing means useful to determine the local condition of the conduit wall. Cable 14 may include one or more electrical conductors or other means for transferring sensor data between the sensors 18 and an external indicating or recording means (not shown).

The sensors 18 are rotatable about a longitudinal axis 16 which coincides substantially with the longitudinal axis of the conduit being measured. This rotatability is achieved in the preferred embodiment by providing a rotatable coupling 13 between a cable portion 12a and a rotatable sensor portion 12b of the carrier 12. Alternative means for allowing rotation of the sensors 18 include a rotatable coupling (not shown) between the carrier 12 and cable 14, or by providing cable 14 with sufficient torsional flexibility for allowing the entire probe 10 to twist relatively freely.

As discussed in the preceding section, it is particularly beneficial to align such sensors 18 with respect to the plane of curvature of a curved section of the conduit under study. For nuclear steam generators utilizing inverted U tubes to provide for the transfer of heat between a circulating primary coolant and a surrounding secondary coolant, it is the innermost and outermost radial portions of the curved conduit segment that are most susceptible to corrosion, stress induced cracking, or other harmful degradation.

The present invention accomplishes this preferential alignment of the sensors 18 by the interaction of an elongated flat strip 20 and the curved conduit interior. The flat strip 20 is secured to the sensor portion 12b of the carrier and is composed of a resilient material which is additionally wear and corrosion resistant, such as nylon, polyethylene, or a tetrofluorocarbon compound. The flat strip 20 may be tapered about the front end 22 to facilitate insertion within the conduit.

Figure 2:
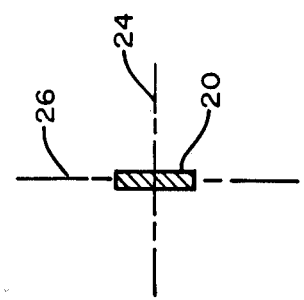
FIG. 2 shows a cross-sectional view of the elongated flat strip as indicated in FIG. 1.

The operation of the flat strip 20 in orienting the sensors 18 within a curved section of conduit is best explained with reference to FIGS. 2 and 3. FIG. 2 shows a cross sectional view of the flat strip 20 as indicated in FIG. 1, clearly showing transverse axes 24 and 26 thereof. As will be appreciated by those knowledgeable in the art of structural mechanics, a member having a cross sectional area such as that of strip 20 possesses two significantly different bending moments with respect to transverse axes 24, 26. The bending moment about the first axis 24 is significantly greater than that about the second, perpendicular axis 26. For a strip 20 constructed from a material such as nylon, these differing bending moments result in a member which is relatively inflexible about axis 24 and relatively easily flexible about axis 26.

Figure 3:
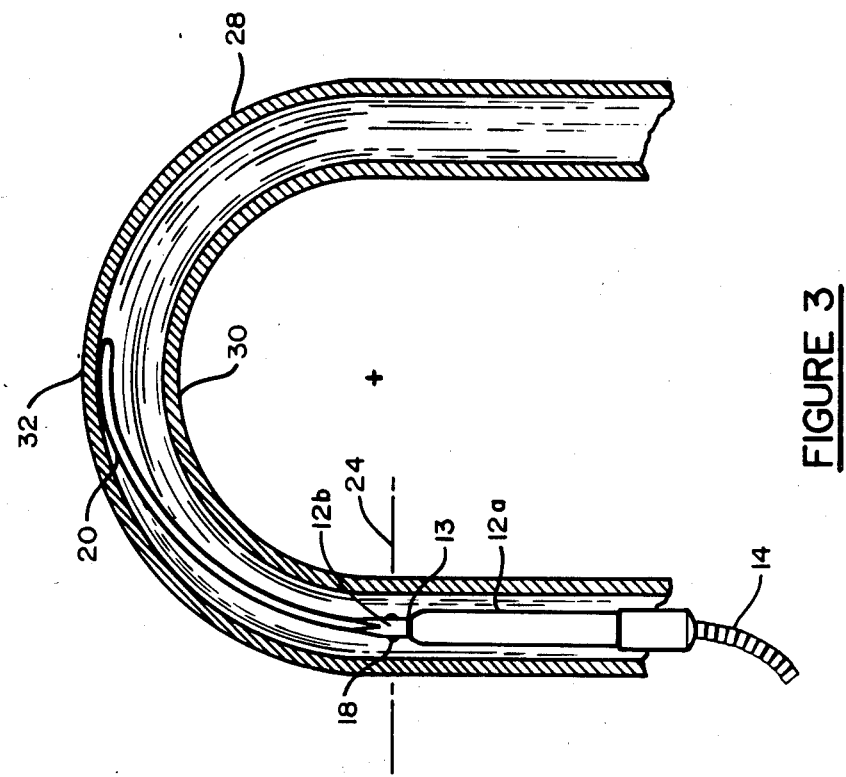
FIG. 3 shows the probe according to the present invention while traversing a cutaway curved section of conduit.

FIG. 3 shows a probe according to the present invention in the process of traversing a curved section of conduit 28. Carrier 12 is pushed longitudinally through conduit 28 by means of the cable 14. Elongated strip 20, preceding the carrier 12 through the conduit 28 encounters the curved portion of the conduit and attempts to conform thereto. As a result of the significant difference between the transverse bending moments about axes 24 and 26, the flat strip 20 will twist both itself and the sensors 18 so as to minimize bending about transverse axis 24 and allow the probe assembly to slip freely along the interior of the conduit 28.

As can be seen in FIG. 3, transverse axis 24 now lies in the plane of curvature of the conduit 28 and results in alignment of sensor means 18 in the desired orientation. For a nuclear steam generator wherein the innermost portion 30 and the outermost portion 32 of the curved conduit are of particular interest, sensor means 18 would be adapted to scan both portions 30, 32 upon proper orientation by the flat strip 20.

The preferred embodiment of the present invention has the advantage of achieving the desired alignment in the curved portion of the conduit 28 without requiring intervention of the probe operator or any other complex orientation detecting means. The probe automatically aligns the sensors 18 upon entry into a curved portion and will realign itself as subsequent curved segments may be entered during a scanning traverse.

Although disclosed hereinabove as being applicable to a nuclear steam generator utilizing an inverted U tube, it will be appreciated that a probe according to the present invention is equally useful for scanning curved conduits of any orientation and configuration, including elbow bends, subsequent bends in transverse directions, and other conduit configurations which may require the use of an oriented scanning probe.

I claim:

1. A self-orienting probe for traversing the interior of a curved conduit, comprising:
    a carrier, including at least a portion rotatable within the conduit about an axis substantially colinear with the longitudinal axis of the conduit;
    means for driving the carrier longitudinally through the conduit;
    an elongated, flat, resilient alignment strip, secured at one end thereof to the rotatable portion of the carrier and extending longitudinally through the interior of the conduit, the strip further having two substantially different bending moments about a first transverse axis and a second transverse axis perpendicular thereto, the strip being more easily deformable about the second axis than about the first axis.

2. The probe as recited in claim 1, wherein the rotatable portion of the carrier further includes
    means for sensing the local wall condition of the curved conduit.

3. The probe as recited in claim 2, wherein the sensing means is an eddy current device.

4. The probe as recited in claim 2, wherein
    the means for driving the carrier longitudinally through the conduit is a flexible cable including at least one conductor between the sensing means and a means for indicating the sensed conduit wall condition, said indicating means located external to said conduit.

* * * * *